United States Patent [19]
Sato et al.

[11] Patent Number: 6,156,318
[45] Date of Patent: Dec. 5, 2000

[54] METHOD OF COUNTERACTING HARMFUL EFFECTS OF HISTAMINE

[75] Inventors: Minoru Sato; Masaaki Takeuchi, both of Miyagi-ken; Naohiko Sato, 32-14 Chofugaoka 2-chome, Chofu-shi, Tokyo, all of Japan

[73] Assignee: Naohiko Sato, Tokyo, Japan

[21] Appl. No.: 09/542,427

[22] Filed: Apr. 4, 2000

Related U.S. Application Data

[63] Continuation-in-part of application No. 09/342,009, Jun. 28, 1999, which is a continuation of application No. 09/038,861, Mar. 11, 1998, Pat. No. 5,958,419.

[30] Foreign Application Priority Data

Mar. 31, 1997 [JP] Japan ........................... 9-94397

[51] Int. Cl.[7] .................................................. D01N 65/00
[52] U.S. Cl. .......................................................... 424/195.1
[58] Field of Search ........................................ 424/195.1

[56] References Cited

U.S. PATENT DOCUMENTS

| | | |
|---|---|---|
| 3,723,410 | 3/1973 | Persinos . |
| 4,082,858 | 4/1978 | Morita et al. . |
| 4,361,697 | 11/1982 | Dobberstein et al. . |
| 4,599,403 | 7/1986 | Kumar . |
| 5,112,610 | 5/1992 | Kienle . |
| 5,250,301 | 10/1993 | Dozono . |
| 5,262,161 | 11/1993 | Dozono . |
| 5,635,611 | 6/1997 | Ishiguro et al. . |
| 5,958,419 | 9/1999 | Sato et al. ........................ 424/195.1 |

FOREIGN PATENT DOCUMENTS

| | | |
|---|---|---|
| 525740 | 2/1993 | European Pat. Off. . |
| 8325156 | 12/1996 | Japan . |

OTHER PUBLICATIONS

Database WPI Section Ch, Week 9805, Derwent Publications Ltd., London, GB; AN 98–042992, XP002064307 & CN 1 137 381 A (Beijing Ultramicrobiological Prod Co Ltd)*abstract*.

Database WPI Section Ch, Week 9712, Derwent Publications Ltd., London, GB; AN 97–119937, XP002064308 & CN 1 080 864 A(Shenyang College Pharmacy)*abstract*.

Database WPI Section Ch, Week 9718, Derwent Publications Ltd., London, GB; AN 97–197202, XP002064309 & JP 09 052 827 A (Taisho Pharm Co Ltd)*abstract*

Patent Abstracts of Japan vol. 097, No. 004, Apr. 30, 1997 & JP 08 325156 A (Ichimaru Pharcos Co Ltd), Dec. 10, 1996, *abstract*.

*Primary Examiner*—Herbert J. Lilling
*Attorney, Agent, or Firm*—Jordan and Hamburg LLP

[57] ABSTRACT

Harmful effects of histamine are counteracted by the administration of an antihistaminic substance comprising a water extract of a plant tissue of Stevia. Standing of the extract naturally cause fermentation to form one or more organic acids, such as lactic acid and acetic acid, thereby enhancing the antihistaminic action. The addition of at least one organic acid to the extract immediately after extraction can also enhance the antihistaminic action.

5 Claims, 4 Drawing Sheets

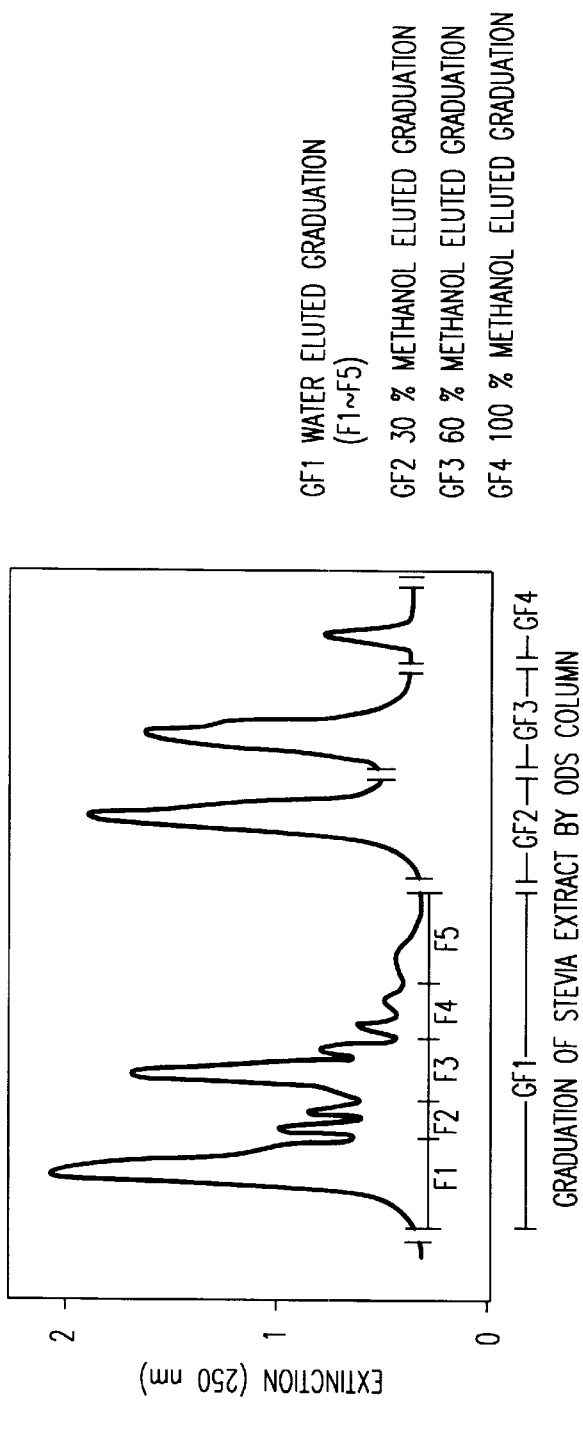
FIG.4 GRADUATION OF STEVIA EXTRACT BY ODS COLUMN
GF1 WATER ELUTED GRADUATION (F1~F5)
GF2 30 % METHANOL ELUTED GRADUATION
GF3 60 % METHANOL ELUTED GRADUATION
GF4 100 % METHANOL ELUTED GRADUATION
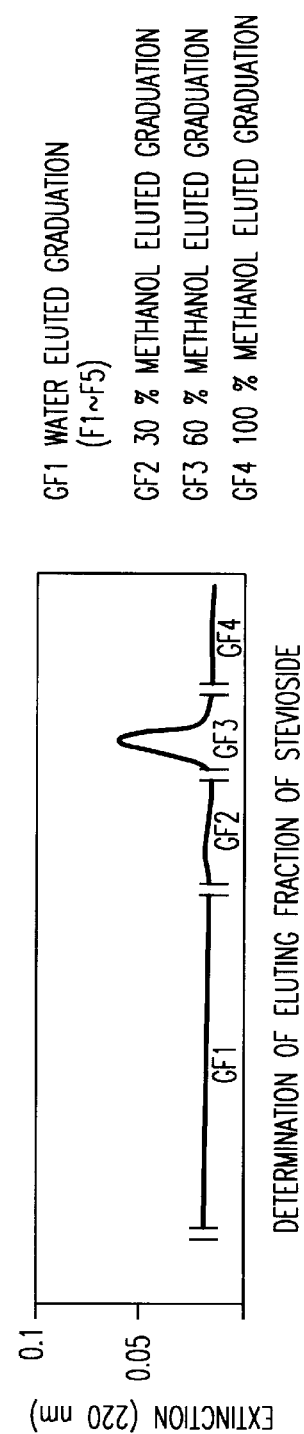
FIG.5 DETERMINATION OF ELUTING FRACTION OF STEVIOSIDE
GF1 WATER ELUTED GRADUATION (F1~F5)
GF2 30 % METHANOL ELUTED GRADUATION
GF3 60 % METHANOL ELUTED GRADUATION
GF4 100 % METHANOL ELUTED GRADUATION

METHOD OF COUNTERACTING HARMFUL EFFECTS OF HISTAMINE

REFERENCE TO RELATED APPLICATIONS

This is a continuation-in-part of application Ser. No. 09/342,009, filed Jun. 28, 1999, which is a continuation of application Ser. No. 09/038,861, filed Mar. 11, 1998, now U.S. Pat. No. 5,958,419, the specification of which is hereby incorporated herein by reference.

BACKGROUND OF THE INVENTION

The present invention relates generally to a method of counteracting harmful effects of histamine. More specifically, a method of counteracting the harmful effects of histamine by the administration of an antihistaminic substance of Stevia origin having the action of repressing various harmful effects to humans and animals is disclosed.

Recently, pollen has been produced in large amounts by excessive tree planting of Japanese cedars and Japanese cypresses. Moreover, industrialization has increased air pollution or the amount of chemical substances released, so that pollenosis, which is an allergic disease due to combined pollution of the chemical substances and the pollen, has been widely spread. Against such an allergic disease, masks are worn. However, the wearing of masks is only symptomatic therapy, and it is impossible to prevent infection through eyes which cannot be covered with masks.

On the other hand, stevioside and rebaudioside, primarily contained in leaves of Stevia, have a strong sweet taste in small amounts, and are used as natural sweeteners low in calories in substitution for sugar. Stevia is therefore known as a raw material for natural sweeteners low in calories.

As oral drugs antagonistic against histamine, drugs containing antihistaminic agents, such as diphenhydramine hydrochloride and promethazine, are commercially available. However, the antihistaminic agents generally have the side effect of causing drowsiness, which results in a decisive disadvantage when an individual tries to tackle work or to study enthusiastically.

The term "histamine" as used in the present application is intended to be inclusive of histaminic substances, namely, chemical mediators, such as histamine and leukotriene, released from special cells, such as mast cells, as a result of the antigen-antibody reaction, and derivatives of histamine. The derivatives of histamine include, for example, dizzerosine produced by elimination of $NH_3$ from histamine and L-lysine. Excessive release of these substances from the cells and activation thereof causes vasodilatation, which is said to be responsible for flare, itch, and pain.

Antihistaminic substances are known. An example is a Japanese Patent Application No. 7-159971, published in 1996, that teaches that stevioside has an activity suppressing the release of histamine in vivo. Stevioside is the sweet ingredient in leaves of Stevia.

On the other hand, the administration of the Stevia extract of the present invention counteracts the harmful effects of histamine in vivo. Thus, the claimed invention differs from the aforementioned prior art in that the antihistaminic mechanisms are different from one another.

It is desirable to have substances of natural origin for relieving, preventing, and/or curing symptoms of allergic conditions or diseases, which have no side effect such as drowsiness, and which can be continuously applied and/or administered without anxiety of a side effect.

SUMMARY OF THE INVENTION

An object of the present invention is to solve the above-mentioned problems and to provide a method of counteracting the harmful effects of histamine by the administration of an antihistaminic substance of natural origin having minimal or no side effects. The administration of antihistamine of the present invention is to be distinguished from the administration of antihistamines which merely provide symptomatic relief or suppress the release of histamine. In contrast thereto, administration of the antihistamine of the invention counteracts the harmful effects of histamine.

According to the present invention, there is provided a method of counteracting the harmful effects of histamine by the administration of an antihistaminic substance comprising a water extract from a plant tissue of Stevia. A method of administering the extract is oral ingestion, though the present invention is not limited thereto. The substance having an antihistaminic action in vivo is a component contained in the plant tissue of Stevia, primarily in its stems and leaves, and contained in water extract thereof. Standing of the extract naturally causes fermentation to form one or more organic acids, such as lactic acid and acetic acid, thereby enhancing the antihistaminic action. The addition of at least one organic acid to the extract immediately after extraction can also enhance the antihistaminic action.

By using an extract from the plant tissue of Stevia of the present invention, the harmful effects to humans and animals caused by excessive release of histamine can be repressed. Hereinafter, the term "animals" is intended to be inclusive of humans.

BRIEF DESCRIPTION OF THE DRAWINGS

FIG. 4 is a graph showing the graduation of Stevia extract by ODS reverse column chromatography.

FIG. 5 is a graph showing the determination of an eluting fraction of stevioside.

DETAILED DESCRIPTION OF THE INVENTION

Figure 1:
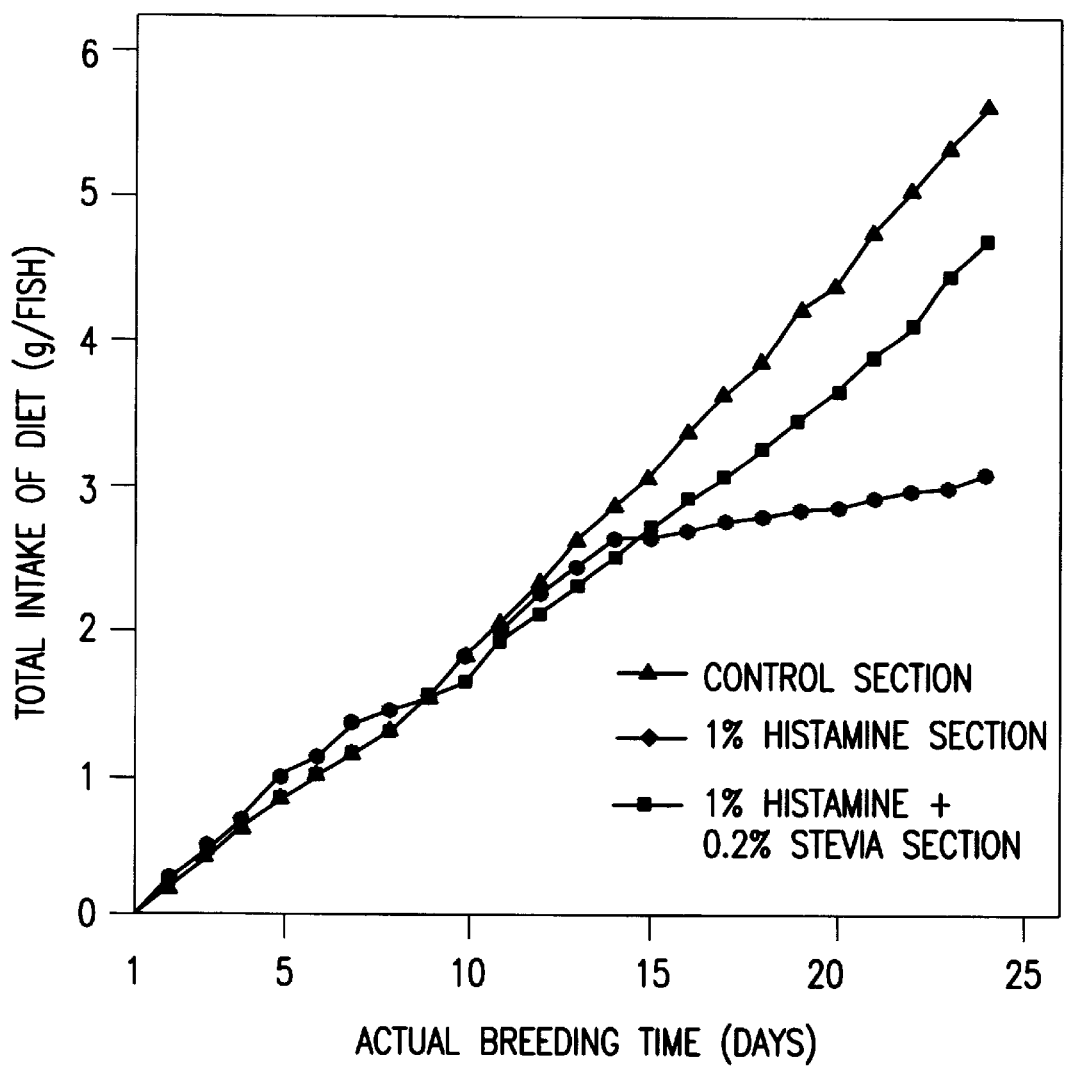
FIG. 1 is a graph showing the relationship between the total intake of rainbow trouts of a diet (g/fish) and the actual breeding time (days) thereof for each test section.

Stevia used as a raw material in the present invention means Stevia rehaudiana Bertoni, a perennial composite originally coming from South America, and relative plants thereof. As stated in parent application Ser. No. 09/038,861, now U.S. Pat. No. 5,958,419, experiments have revealed that the unidentified substance therein which has antihistaminic activity in that it counteracts the harmful effects of histamine is mostly contained in the leaves and stems, particularly in the stems before formation of buds and in the stems of mature plants, but also in roots, flowers andjuvenile plants. Further, the antihistaminic effect has not been observed in steviocide and rebaudioside known as the sweetening components of Stevia.

When the method of the present invention is to be applied to humans and animals, all of the tissues of the plant, preferably the leaves of Stevia or the stems before formation of buds, are harvested, and pulverized after drying or without drying, followed by extraction. They may be pulverized and extracted simultaneously with harvest. In order to improve the extraction efficiency, it is preferred that they are cut and thereafter further pulverized. In general, the roots are not used for germination in the coming spring.

The active substance, the chemical composition and structure of which have not been determined, is contained in high concentration in a supernatant (i.e., extract) obtained after the plant tissue has been immersed in water at normal room temperature (e.g., 20–22° C.) for 2 to 3 days. It is also contained in high concentration in a supernatant (i.e., extract) obtained by immersing the plant tissue in warm water at 30° C. to 50° C. for 3 hours and in an extract obtained by boiling it in hot water.

To provide a stock solution of sufficient concentration that its bottling or containerizing, shipping, storage and use are convenient, the extract of Stevia is concentrated to form a stock solution (i.e., stock extract) having a solids content of about 16 to 20% by weight. In general, 0.3 liter to 3 liters of the stock solution is obtained from 1 kg of the mixture of dried stems and leaves of Stevia.

The stock solution of the plant tissue of Stevia is neutral. When the stock solution is stored in a container at normal room temperature (about 20 to 22° C.), spores of yeast existing in the plant tissue of Stevia germinate and ferment to fill the container with carbon dioxide. Accordingly, the stock solution is preferably stored in a container equipped with a device for automatically releasing carbon dioxide when the internal pressure reaches a specified value.

Organic acids, such as acetic acid and lactic acid, are produced by fermentation, and a synergistic effect thereof with the extracted antihistaminic component of Stevia enhances the effective antihistaminic action. The antihistaminic action can be further enhanced by addition of organic acid to the extract of Stevia after fermentation. Further, the antihistaminic action can also be enhanced by addition of an organic acid to the solution immediately after extraction.

The organic acids that may be added to the extract include acetic acid, lactic acid, propionic acid, valeric acid, citric acid, tartaric acid, malic acid, maleic acid, fumaric acid and acrylic acid.

EXAMPLE 1

(1) Preparation of Test Solution of Stevia

In the spring, nursery stocks of Stevia were planted, and above-ground parts were harvested before formation of buds. After harvest, the above-ground parts were divided into leaves and stems. The leaves were finely pulverized with a pulverizer to produce a Stevia leaf powder, and the stems were cut to a size of about 5 cm and then finely pulverized with a pulverizer to produce a Stevia stem powder.

The Stevia leaf and stem powders thus obtained were compounded at a weight ratio of 3:7, and homogeneously mixed. The resulting Stevia mixed powder was used as a raw material for Stevia extract stock solution.

Then, 1 kg of the Stevia mixed powder was boiled in 10 liters of water for 1 hour. After cooling, the powder was squeezed with a squeezing machine, and the squeezed powder was removed, followed by boiling down of the liquid for 3 hours to obtain 1.2 liters of an unfermented Slevia extract stock solution. The unfermented extract stock solution was stored in a container, and allowed to stand at 20–30° C. As a result, fermentation proceeded, and intermittent discharge of carbon dioxide was required.

The fermentation proceeds with violence in the early stages, and gradually becomes gentle after an elapse of 3 to 4 months. Even after an elapse of 1 year, the fermentation further continues for 3 years or more.

In this example, a Stevia extract stock solution fermented for 1 year was used. Accordingly, the Stevia solution in this example corresponds to 1.2 $g/cm^3$ of the raw material, Stevia mixed powder. Further, the Stevia solution has a solids concentration of about 20% by weight.

(2) Breeding of Rainbow Trouts

Rainbow trouts were bred under the following conditions:

Average weight at the start of breeding: 4.84 g

Breeding water temperature: 15±1° C.

Breeding fish tank: Plastic tank having an internal volume of 36 liters

Flow rate of water: 250 ml/minute

Number of fishes bred: 20 fishes/test section

Method of feeding: 3 times daily until satiation

Composition of Test Diets

A commercial diet for rainbow trouts was purchased, and after pulverization, an additive or additives for testing were added thereto, followed by mixing. The mixture was reformed, and then given to the rainbow trouts. A diet containing no additive was also once pulverized and reformed.

Control Section: No additive was added to the commercial diet for rainbow trouts.

1% Histamine Section: One part by weight of histamine was added to 100 parts by weight of the commercial diet for rainbow trouts.

1% Histamine+0.2% Stevia Section: One part by weight of histamine and 0.2 part by weight (in terms of solid matter) of the Stevia test solution were added to 100 parts by weight of the commercial diet for rainbow trouts.

(3) Results of Test

With respect to the total intake of the diet per rainbow trout, 13 to 15 days after the start of breeding, the diets were satisfactorily ingested in all the sections, and no significant difference was observed between the different sections. However, after an elapse of about 15 days, the diet was well taken in the control section, whereas the diet was little taken in the 1% histamine section. On the other hand, the ingestion of the diet continued in the 1% histamine+0.2% Stevia section although inferior to that in the control section.

For each test section, the relationship between the total intake of the diet and the actual breeding time (days) is shown in FIG. 1.

Figure 2:
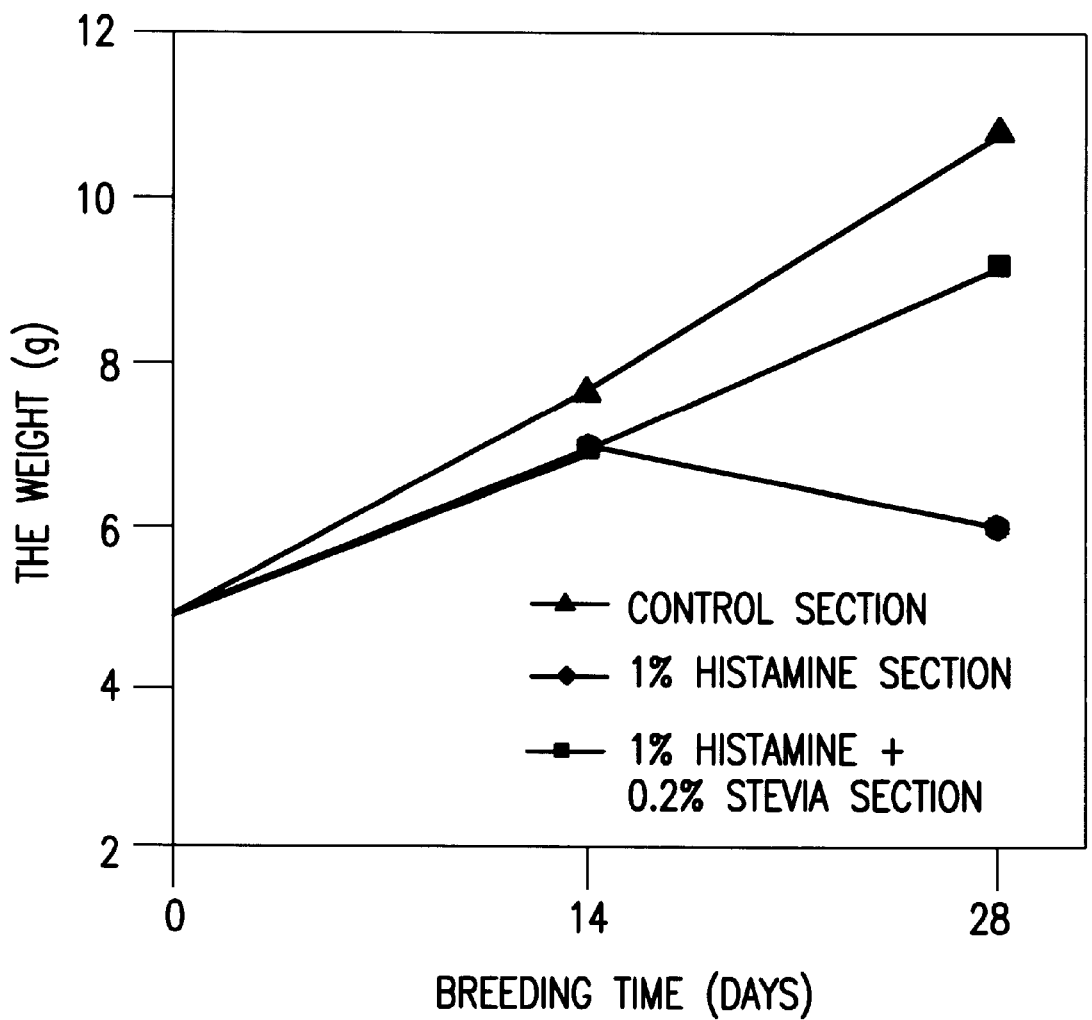
FIG. 2 is a graph showing the relationship between the breeding time (days) of rainbow trouts and the weight thereof for each test section.

At the same time, changes in weight with the breeding time (days) of the rainbow trouts were measured. Results thereof are shown in Table 1, and for each test section, the relationship between the breeding time and the weight is shown in FIG. 2. Further, the weight the rainbow trouts and the standard deviation thereof in each test section after breeding for 28 days are shown in FIG. 3.

TABLE 1

| Breeding (days) | Control Section | | 1% Histamine Section | | 1% Histamine + 0.2% Stevia Section | |
|---|---|---|---|---|---|---|
| | Average Weight (g) | Standard Deviation | Average Weight (g) | Standard Deviation | Average Weight (g) | Standard Deviation |
| 0 | 4.82 | 0.19 | 4.86 | 0.21 | 4.83 | 0.20 |
| 14 | 7.68 | | 6.98 | | 6.88 | |
| 28 | 10.93 | 1.2 | 6.09 | 0.57 | 9.28 | 2.24 |

Figure 3:
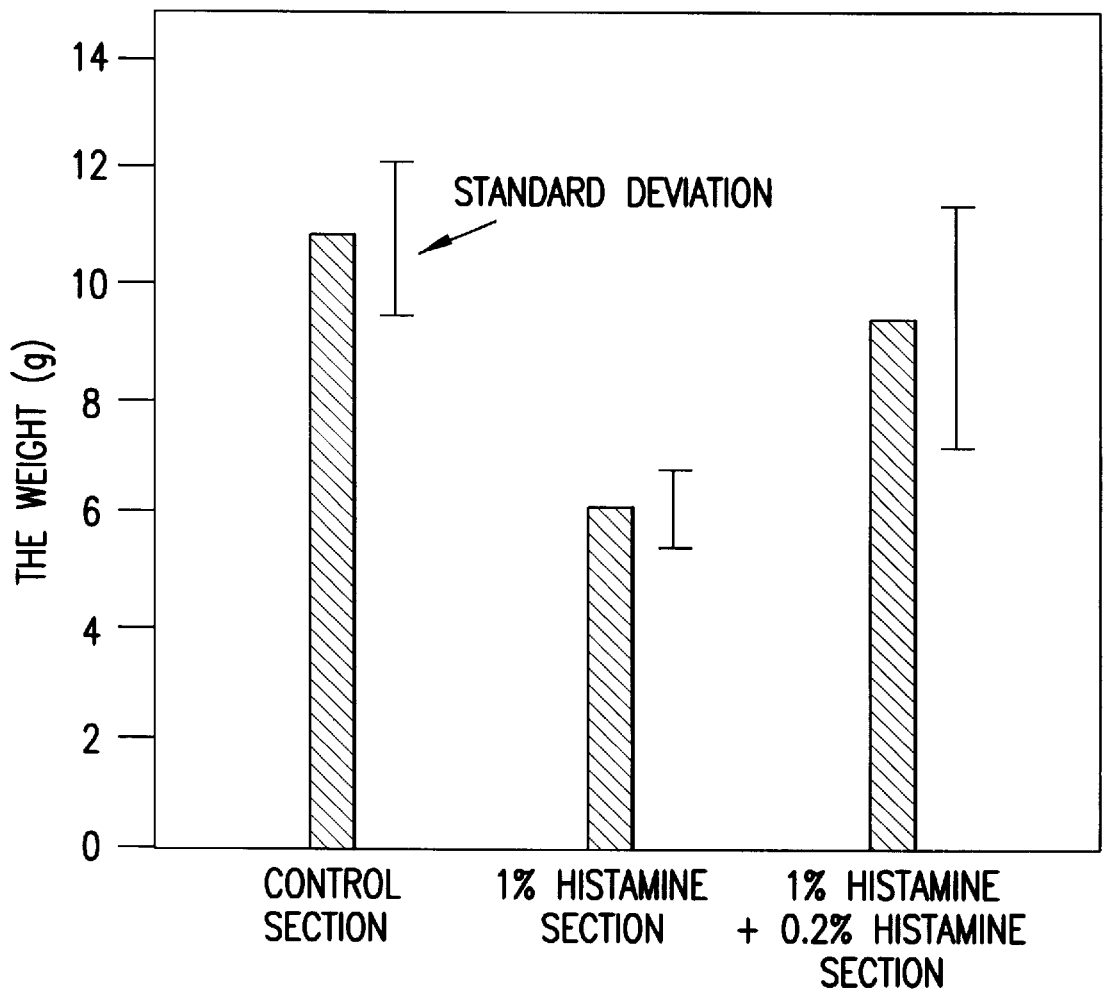
FIG. 3 is a graph showing the weight of rainbow trouts and the standard deviation thereof after breeding for 28 days for each test section.

Table 1 and FIGS. 1 to 3 show that a substance antagonistic against the action of histamine exists in the test solution of Stevia. At the same fine, from the fact that the standard deviation in the 1% histamine+0.2% Stevia section is large, it is understood that the difference in the antihistaminic effect of Stevia between individuals is significant.

These rainbow trouts were dissected, the stomachs were fixed in BOUIN solution (picric acid saturated solution: formalin: glacial acetic acid=15:5:1), embedded in paraffin wax, sectioned and stained with hematoxylin and eosin for optical microscopic observation.

In the control section, muscular layers and mucosal cells of the stomach walls in the pyloric regions were well developed, and lamina propria mucosac for supplying nutrients to the mucosal cells well extended from the muscular layers to the vicinities of leading edges of the mucosal cells. On the other hand, in the 1% histamine section, the leading edges of almost all mucosal cells were deficient. Although not deficient, the lamina propria mucosae atrophied, and the damage of tissues was observed at the leading edges of the mucosal cells. Thereafter, the decay of the tissues conceivably takes place, and it is clear that histamine is responsible for the atrophy of the lamina propria mucosac and the decay of the mucosal cells.

In the 1% histamine+0.2% Stevia section, the leading edges of the mucosal cells were scarcely deficient, and the lamina propria mucosae well extended to the leading edges of the mucosal cells.

In the 1% histamine section, crevices were observed in the mucosal cell layers in the cardiac regions, and the atrophy of the mucosal cells was observed. In the control section and the 1% histamine+0.2% Stevia section, the states of the mucosal cells were normal. In general, the deficiency of the stomach walls caused by histamine was noticeable in the pyloric regions and was slight in the cardiac regions.

The above-mentioned results revealed that the Stevia test solution had the action of repairing the atrophy, damage and decay of the tissues caused by histamine.

EXAMPLE 2

(1) Preparation of Test Solution of Stevia

The water extract of Stevia was graduated into fractions by means of reverse column chromatography. The column has a diameter of 2 cm and a height of 30 cm, filled with ODS-AM 120-S50 (YMC Co. LTD.). First, the Stevia extract was poured into the top of the column and the components were eluted by water. The first eluted fraction was named F-1, the second was named F-2, the third was named F-3, the fourth was named F-4, and the fifth was named F-5. After F-5 was eluted, the column was eluted with aqueous methanol solution of 30%, by weight, methanol concentration ("30% methanol") and the fraction was named F-6. After F-6 was eluted, the column was eluted with aqueous methanol colution of 60%, by weight, methanol concentration ("60% methanol") and the fraction was named F-7. And after F-7 was eluted, the column was eluted with 100% methanol and the fraction was named F-8.

To determine the position of stevioside in the same column accurately, 1% solution of stevioside was poured first, instead of the Stevia extract, into the same column and eluted with water, 30% methanol, 60% methanol and 100% methanol in the same way as the graduation of the Stevia extract. The results are shown in FIGS. 4 and 5. From FIGS. 4 and 5 below, it can be concluded that stevioside in the water extract of Stevia is included in F-7.

(2) Breeding of Rainbow Trouts

Rainbow trouts were bred under the following conditions:

Average weight at the start of breeding: 3.85 g

Number of fishes bred: 20 fishes/test section

Days of breeding: 28 days

Stevia solution: hot water extract of Stevia, followed by fermentation, and concentration to a solids content of about 20%, by weight.

TABLE 4

| Test Section | Content of the Diet |
| --- | --- |
| 1 | Commercial diet for rainbow trouts |
| 2 | Diet of Test Section 1 + 1% of histamine |
| 3 | Diet of Test Section 1 + 1% of histamine + 2000 ppm of Stevia extract |
| 4 | Diet of Test Section 1 + 1% of histamine + F-1 |
| 5 | Diet of Test Section 1 + 1% of histamine + F-2 |
| 6 | Diet of Test Section 1 + 1% of histamine + F-3 |
| 7 | Diet of Test Section 1 + 1% of histamine + F-4 |
| 8 | Diet of Test Section 1 + 1% of histamine + F-5 |
| 9 | Diet of Test Section 1 + 1% of histamine + F-6 |
| 10 | Diet of Test Section 1 + 1% of histamine + P-7 |
| 11 | Diet of Test Section 1 + 1% of histamine + F-8 |

A commercial diet for rainbow trout was purchased, and after pulverization, the respective additives for testing were added, followed by mixing. The mixture was reformed, and then given to the rainbow trouts. In Table 4, the commercial diet for rainbow trout of test section 1 was purchased and reformed without mixing any additives. In test sections 4 to 11, the solids content of each fraction was controlled to be 400 ppm.

After the breeding, the rainbow trouts were dissected, the stomachs were fixed with BOUIN solution, embedded in paraffin wax, sectioned and stained with hematoxylin and eosin for optical microscopic observation of the mucous membranes.

From the microscopic observation, test sections 1, 3 and 5 are quite normal, and test section 2 is naturally inflamed. This phenomenon means that the harmful action of histamine is counteracted by Stevia extract, and the effective ingredient of the Stevia extract is mostly in F-2. In other test sections, disorders of the mucous membrane were observed, especially in test sections 8 and 10, the atrophy of the lamina propria mucosae is remarkable, and the tops of the mucosal cells are lost in the cardiac region of the stomachs of the rainbow trouts, and the mucosal cells are lost in the pyroric region of the stomachs.

Enlarged color photographs of the cardiac region of the stomachs of the rainbow trouts were taken. Test section 1 showed a normal cardiac region, the mucosal cells and mucous layer being arranged in good order and the lamina propria mucosae extending to the tops. In test section 2, the atrophy of the lamina propria mucosae was remarkable, the mucosal cells not being arranged in order, and the swelling of the mucous layer was observed on account of the action of histamine. In test section 5, the harmful action of histamine is suppressed almost completely. However, in test section 10, the atrophy of the lamina propria mucosae is remarkable, the tops of the mucosal cells are broken, and the arrangement of the mucosal cells is out of order.

From these experiments, the following conclusion is obtained. That is, the most effective substance or substances exist in F-2, and stevioside, which chiefly exists in F-10, is not as effective as the Stevia extract of the present invention. Stevioside does not counteract the harmful effects of histamine.

What is claimed is:

1. A method of counteracting effects of histamine comprising administering an antihistaminic composition comprising a water extract of Stevia.

2. The method according to claim 1, wherein said extract is a fermented extract.

3. The method according to claim 1 or 2, wherein said extract is of a plant tissue of Stevia selected from the group consisting of stems and leaves.

4. The method according to claim 1 or 2, wherein said composition further comprises an organic acid.

5. The method according to claim 4, wherein said organic acid is selected from the group consisting of acetic acid, lactic acid, propionic acid, valeric acid, citric acid, tartaric acid, malic acid, maleic acid, fumaric acid and acrylic acid.

* * * * *